United States Patent [19]

Platsoucas

[11] Patent Number: 4,988,676

[45] Date of Patent: Jan. 29, 1991

[54] CELLULAR PROLIFERATION T CELL SUPPRESSOR FACTOR

[75] Inventor: Chris Platsoucas, Houston, Tex.

[73] Assignee: Sloan-Kettering Institute for Cancer Research, New York, N.Y.

[21] Appl. No.: 218,620

[22] Filed: Jul. 13, 1988

Related U.S. Application Data

[63] Continuation-in-part of Ser. No. 609,273, May 11, 1984, abandoned.

[51] Int. Cl.$^5$ .............................................. A61K 37/02
[52] U.S. Cl. ...................... 514/21; 424/534; 435/29; 514/2; 530/350; 530/351; 530/837
[58] Field of Search ........................ 424/181, 85, 95; 435/68, 29; 530/350, 351, 837; 514/2, 21

[56] References Cited

U.S. PATENT DOCUMENTS

| | | | |
|---|---|---|---|
| 4,464,355 | 8/1984 | Fabricius et al. | 424/101 |
| 4,468,379 | 8/1984 | Gottlieb | 424/101 |
| 4,486,409 | 12/1984 | Goldfarb | 424/85 |

OTHER PUBLICATIONS

Grillot-Courvalin, C. and J. C. Brouet, Nature 292:844 (1981).
Greene, Warner C. et al., J. Immunol. 129(5):1986 (1982).
Taussig, M J. et al., Nature 277:305 (1979).
Taussig, M. J. et al. Nature 277:308 (1979).
Kontiainen, Sirkka et al., Nature 274:477 (1978).
Eisenthal, A. et al. Ann N.Y. Acad. Sci. 332:367 (1979).
Smith, R. T. et al., Am. J. Pathol. 60:495 (1970).
Jegasothy, B. V. et al., Science 193:1260 (1976).
Lee, S. C. and Z. J. Lucas, J. Immunol. 118(1):88 (1977).
Jegasothy, B. V. et al., J. Exp. Med. 150:622 (1979).
Namba, Y. et al., J. Immunol. 118(4):1379 (1977).
Waksman, B. H. et al., Cell Immunol. 36:180 (1978).

*Primary Examiner*—Sam Rosen
*Attorney, Agent, or Firm*—John P. White

[57] ABSTRACT

New human T cell suppressor factors have been identified which suppress mitogen, antigen or alloantigen driven cellular proliferation of human peripheral blood leukocytes, as well as antibody synthesis and secretion and growth of human tumor cell lines.

Such factors have potential use for the treatment of graft versus host disease, autoimmune disease and lympho-proliferative disorders such as leukemia as well as other malignancies.

10 Claims, 5 Drawing Sheets

CELLULAR PROLIFERATION T CELL SUPPRESSOR FACTOR

The invention described herein was made in the course of work under Grant No. CA 32070 by the National Cancer Institute. The U.S. government has certain rights in this invention.

BACKGROUND OF THE INVENTION

This application is a continuation-in-part of U.S. Ser. No. 609,273 filed May 11, 1984, now abandoned, the contents of which are hereby incorporated by reference into the present disclosure.

The invention relates to factor(s) which suppress cellular proliferation and antibody production and would be useful to control disorders such as those involving abnormal cellular proliferation.

Previous suppressor factors have been reported in the literature [See Grillot-Courvalin, Catherine et al., (1981) Nature 292:844; Greene, Warner C., et al. (1982) J. Immunol, 129:1986; M. J. Taussign, et al. (1979) Nature 277: at 305 and 308; Sirkka Kontianen, et al. (1978) Nature 274:477; Eisenthal, A., et al. (1979) Ann N.Y. Acad. Sci. 332:367; Smith, R. T., et al. (1970) Am. J. Pathol. 60:495; Namba, Y., et al. (1975) Inflammation 1:5; Lee, S. C., et al. (1977) J. Immunol. 118:88; Jegosothy, B. V., et al. (1979) J. Exp. Med. 150:622; Namba, Y., et al. (1977) J. Immunol. 118:1379; Jegosathy, B. V., et al. (1976) Science 193:1260; and Waksman, B. H., et al. (1978) Cell Immunol. 36:180].

The suppressor factor(s) described in the invention and different from all these factors because they: (a) exhibit different functional properties, (b) exhibit different molecular weight; (c) are produced constitutively and in substantially higher quantities.

SUMMARY OF THE INVENTION

The invention provides for a human suppressor factor(s) (SF) isolated from human lymphoblastoid tumor cell supernatant where it is constitutively found. SF is characterized by suppression of mitogen, antigen or alloantigen driven cellular proliferation of human peripheral blood leukocytes as well as suppression of antibody production, synthesis and secretion.

SF has a molecular weight range of 55,000 to 70,000 daltons.

SF suppresses the cellular proliferative response of T and B cells. This suppression of cellular response occurs in the presence of pokeweed mitogen (PWM), concanavalin A (CON A), phytohemagglutinin (PHA) and mixtures thereof.

SF inhibits the proliferative response of human peripheral blood mononuclear leukocytes to allogenic cells in mixed lymphocyte cultures. SF also inhibits the proliferation of tumor cell lines while having no effect on natural killer cell (NK) cytotoxicity.

SF inhibits antibody production in vitro by human peripheral blood mononuclear leukocytes exposed to PWM while not affecting the viability of human peripheral blood mononuclear leukocytes in culture.

SF does not cause lysis of K-562 leukemic cell targets as determined by chromium release assay. SF also does not induce the differentiation of suppressor T-cell.

DETAILED DESCRIPTION OF THE INVENTION

Figure 1A:
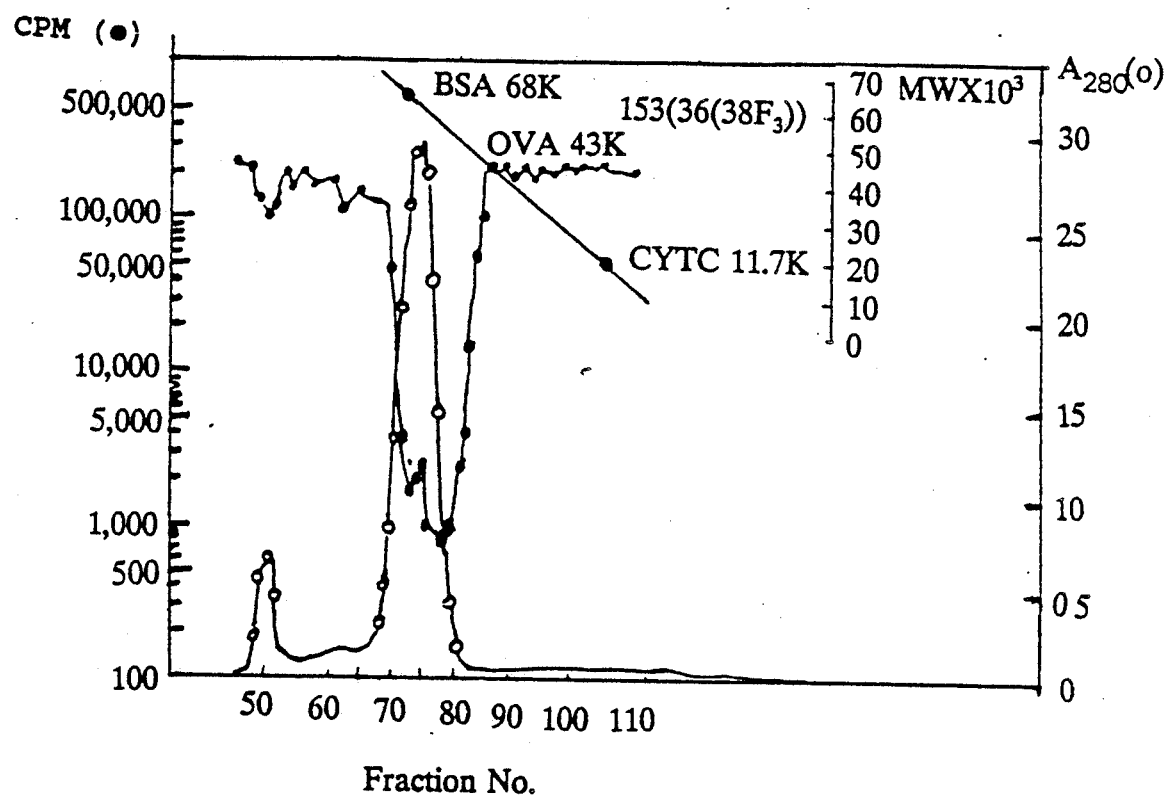
FIG. 1 shows ACA 44 gel filtration chromatography analysis of a) 153 b) 169 and c) Jurkaat suppressor factors. Suppressor activity of the proliferative response of human peripheral blood mononuclear cells to PHA ( ) was found in the range of 50–70 kd. The 160 suppressor factor was eluded in the same range (data not shown).

In the invention factor(s) have been identified which suppress mitogen or antigen (alloantigen) driven cellular proliferation of human peripheral blood leukocytes and antibody production.

Such factor(s) have potential use for example in the treatment of patients with cancer, graft versus host disease(s), autoimmune disease(s) and lymphoproliferative malignancy disorder(s) such as leukemia.

Factor(s) are described and identified in this application, which inhibit leukocyte proliferative responses. In particular these factor(s), suppressor factor (SF), have been found to be produced by hematopoietic cells such as human lymphoblastoid cell lines—especially T cell lines an others such as B cell lines or erythroleukemic cell lines. Particular T cell lines known to produce suppressor factor(s) are Jurkat, HPB-ALL, TALL-1, HD-MAR, SKW-3, DND 41, HPB-MLT and MOLT-4. Erythroleukemic cell lines such as K-562 can also produce SF. B cell lines such as CESS can also produce SF.

Supernatants from such cells inhibit the proliferative responses of T-lymphocytes to mitogens such as phytohemagglutinin (PHA), concanavalin A (CON A) and pokeweed mitogen (PWM). (Tables I-III).

It also inhibits the proliferative responses of T-cells to allogenic cells in mixed lymphocyte culture (MLC). (Table IV).

Also this factor(s) inhibits antibody production of blood cells, and especially in vitro by human peripheral blood mononuclear leukocytes in the PWM-driven system (Table V). SF may inhibit certain proliferative responses of B-cells.

The action of SF appears to be cytostatic, not cytotoxic, since it:

(1) does not affect the viability of human peripheral blood mononuclear leukocytes in culture after a four day incubation (Table VI); and (2) does not cause lysis of K562 leukemic cell targets which can be determined by such assays as the chromium release assay.

This factor(s) does not affect natural killer (NK) cell cytotoxicity against K-562 targets. (Table VII). Also this factor inhibits the growth in vitro of cells from certain human tumor cell lines (lung, colon, etc.) (Table VIII).

These SF(s) exhibit a relative molecular weight in the range of 55–70,000, as determined by AcA-44 gel filtration.

Tables I–III shows the inhibitory effect of SF on the peripheral blood mononuclear leukocyte proliferative response to mitogens CON A, PWM and PHA. In these examples SF is produced by Jurkat, Molt-4, K-562 and HPB-ALL cells as well as other cell lines. In addition, hematopoietic cell hybridomas produce SF. Cess B cell line generally is positive for SF.

Administration in vivo of partially purified preparations of the Jurkat suppressor factor of the subject invention and the 160(36(38F3)) suppressor factor inhibited significantly the primary antibody response of C3H mice to sheep erythrocytes when administered intravenously (see Table IX) or intraperitoneally (data not shown). In contrast, purified preparations of the 169(36(38F3)) suppressor factor had no effect in vivo as anticipated by the in vitro experiments.

The dosages administered were as follows: 2.5 suppressor factor units (SFU) per injection given intravenously on days 1, 2, 3 and 4 in a total volume of 50 microliters. A suppressor factor unit was defined as the reciprocal of the maximum dilution that inhibited by 50% the proliferative response of human peripheral blood mononuclear leuckocytes to PHA.

The Jurkat, 153(36(38F3) and 160(36(38F3)) suppressor factors significantly inhibited the proliferative response of highly purified leukemic B cells from patients with chronic lymphocytic leukemia to preparations containing B-cell growth factor (BCGF), anti-immunoglobulin M (anti-M) and/or Staphylococcus aureas Cowans I (SAC) (see Table X).

Figures 3A, 3B, 3C:
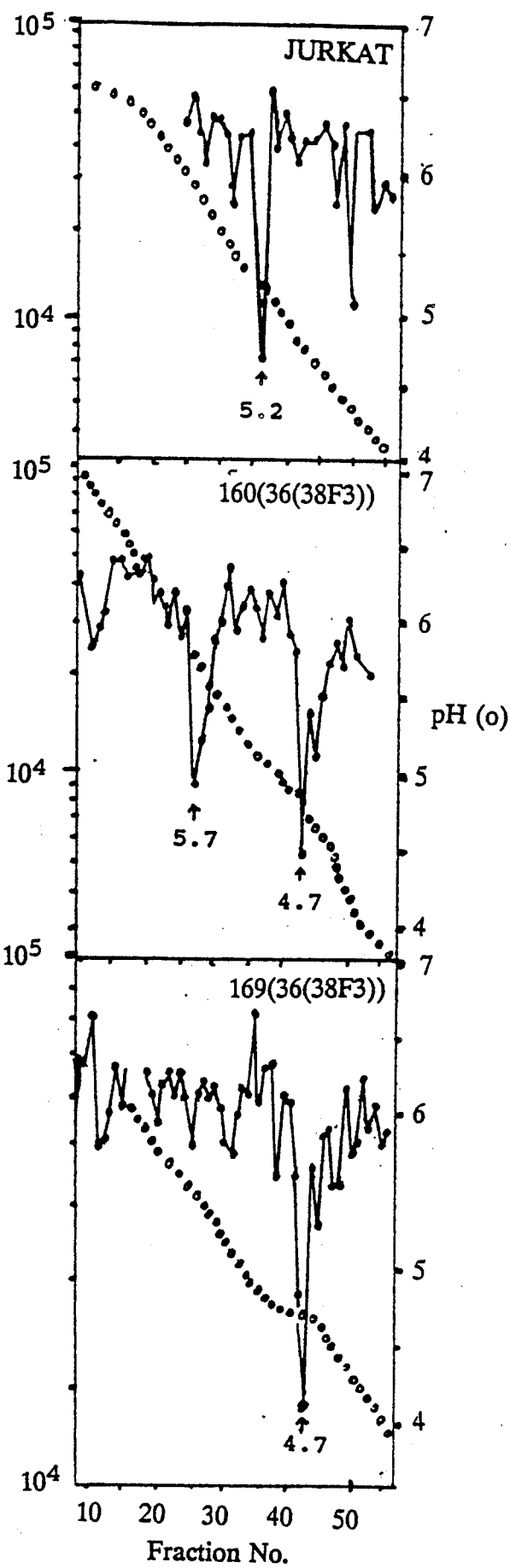
FIG. 3 shows chromatofocusing of the (a) Jurkat b) 160 and (c) 169 suppressor factors. Proliferative response to PHA is plotted against fraction number.

The Jurkat suppressor factor is different from the 160(36(38F3) suppressor factor because:

(a) the Jurkat suppressor factor significantly inhibits in vitro CFU-C, whereas the 160(36(38F3) suppressor factor does not (see Table XI); and (b) the Jurkat suppressor factor has an isoelectric point of 5.2, whereas the 160(36(38F3) suppressor factor has two isoelectric points of 5.7 and 4.7 (see FIG. 3).

The Jurkat suppressor factor is different from the 169(36(38F3)) suppressor factor because:

(a) the Jurkat suppressor factor inhibits in vitro CFU-C, whereas the 169(36(38F3)) suppressor factor does not (see Table XI); and (b) the Jurkat suppressor factor has an isoelectric point of 5.2, whereas the 169(36(38F3)) suppressor factor has an isoelectric point of 4.7 (see FIG. 3).

The Jurkat suppressor factor, the 169(36(38F3)) suppressor factor and the 77(38F3) suppressor factor are different because the Jurkat suppressor factor suppresses in vitro proliferative responses of mouse splenocytes and thymocytes, whereas the 169(36(38F3)) suppressor factor and the 77(38F3) suppressor factor do not (see Tables XII and XIII);

The above inherent characteristics of the suppressor factors clearly demonstrate that:

(a) the Jurkat suppressor factor of the subject application is useful to inhibit immunological responses in vivo; and (b) the Jurkat suppressor factor of the subject application is different from the T-T cell hybridoma suppressor factors.

The examples illustrated in the tables are for illustrative purposes only and are not meant to limit the invention to the examples shown. It is noted that the invention is not limited to one single suppressor factor but it is believed that SF may be more than one molecule or molecular form or, different cell lines produce different suppressor factors exhibiting similar or partially similar properties.

SF can be useful in treating or preventing graft versus host disease, also in patients who have received heterologous or autologous transplants whether of bone marrow, kidney, heart, etc. Also it would be useful in treating autoimmune diseases such as Systemic Lupus Erythematosus, Myasthenia Gravis, Rheumatoid Arthritis, Multiple Sclerosis and Allergies. SF has applications in the treatment of lympho-proliferative disorders such as leukemia as well as in the treatment of other malignancies, including human solid tumors such as lung, colon, etc.

TABLE IA

Inhibition of proliferative response of peripheral blood mononuclear leukocytes to PHA, by SF produced by the Jurkat, HPB-All and Molt 4 lines

| | PROLIFERATIVE RESPONSES (CPM) | | | | | |
|---|---|---|---|---|---|---|
| | Jurkat | | HPB-All | | Molt-4 | |
| % SF (v/v) | CPM | % suppression | CPM | % suppression | CPM | % suppression |
| medium | 513 ± 175 | — | 513 ± 175 | — | 513 ± 175 | — |
| medium + PHA | 11058 ± 1883 | — | 11058 ± 1883 | — | 11058 ± 1883 | — |
| medium + PHA +0.015% SF | 2351 ± 223 | 79% | 6318 ± 1689 | 43% | 2399 ± 339 | 78% |
| medium + PHA +0.05% SF | 2612 ± 337 | 76% | 2199 ± 1792 | 35% | 1118 ± 28 | 89% |
| medium + PHA +0.1% SF | 2861 ± 269 | 74% | 8800 ± 2172 | 20% | 998 ± 105 | 91% |
| medium + PHA +0.5% SF | 4404 ± 390 | 60% | 1778 ± 111 | 84% | 1333 ± 328 | 88% |
| medium + PHA +0.95% SF | 3921 ± 277 | 65% | 1419 ± 234 | 87% | 1127 ± 77 | 89% |
| medium + PHA +1.9% SF | 4156 ± 256 | 62% | 1564 ± 156 | 86% | 1130 ± 138 | 89% |
| medium + PHA +3.75% SF | 4426 ± 354 | 60% | 2186 ± 265 | 80% | 1240 ± 82 | 89% |
| medium + PHA +15% SF | 3512 ± 302 | 68% | 2335 ± 319 | 79% | 985 ± 36 | 91% |
| medium + PHA +30% SF | 3538 ± 571 | 68% | 2685 ± 236 | 76% | 728 ± 57 | 93% |

TABLE IB

Inhibition of proliferative response of peripheral
blood mononuclear leukocytes to PHA, by SF produced
by the K562, HPB-All, Molt 4 and CESS tumor cell lines
PROLIFERATIVE RESPONSES (CPM)

| % SF (v/v) | K562 CPM | % suppression | Molt-4 CPM | % suppression | Cess CPM | % suppression | HPB-LL CPM | % suppression |
|---|---|---|---|---|---|---|---|---|
| medium | 2279 ± 14 | — | 2279 ± 14 | — | 2279 ± 14 | — | 2279 ± 14 | — |
| medium + PHA | 56211 ± 3811 | — | 56211 ± 3811 | — | 56211 ± 3811 | — | 56211 ± 3811 | — |
| medium + PHA +1.87% SF | 1624 ± 88 | 97% | 1499 ± 248 | 97% | 48729 ± 4699 | 13% | 8124 ± 399 | 86% |
| medium + PHA +3.75% SF | 1515 ± 190 | 97% | 1287 ± 130 | 98% | 51048 ± 6139 | 9% | 8109 ± 816 | 86% |
| medium + PHA +7.5% SF | 2091 ± 942 | 96% | 1249 ± 132 | 98% | 53579 ± 3152 | 5% | 6687 ± 773 | 88% |
| medium + PHA +15% SF | 1536 ± 119 | 97% | 1225 ± 143 | 98% | 59898 ± 5211 | 6% | 7916 ± 1116 | 86% |
| medium + PHA +30% SF | 2009 ± 254 | 96% | 865 ± 101 | 98% | 31823 ± 1550 | 43% | 5434 ± 777 | 90% |

TABLE 1C

Inhibition of proliferative response of human peripheral
blood mononuclear leukocytes to PHA, by SF produced
by TALL-1, HD-Mar, SKW-3, DND-41 and HPB-MLT

| | Cell line Supernatant** | CPM | % Suppression |
|---|---|---|---|
| MNC* | None | 4677 ± 1367 | |
| MNC + PHA | None | 93646 ± 9369 | |
| MNC + PHA | TALL-1 | 18119 ± 3822 | 81 |
| MNC + PHA | HD-Mar | 9914 ± 1182 | 89 |
| MNC + PHA | SKW-3 | 9268 ± 434 | 90 |
| MNC + PHA | DND-41 | 28633 ± 3356 | 69 |
| MNC + PHA | HPB-MLT | 12136 ± 342 | 87 |

*MNC: Human, peripheral blood mononuclear leukocytes.
**Cell line supernatants were employed at concentration of 25% (v/v).

TABLE III

Inhibition of proliferative response of peripheral
blood mononuclear leukocytes to PWM by SF produced
by the Jurkat tumor cell line

| | PROLIFERATIVE RESPONSES (CPM) Jurkat | |
|---|---|---|
| % SF (v/v) | CPM | % suppression |
| Medium | 703 ± 84 | — |
| Medium + PWM | 13119 ± 1792 | — |
| Medium + PWM +1.56% SF | 4631 ± 389 | 65% |
| Medium + PWM +3.12% SF | 4560 ± 373 | 65% |
| Medium + PWM +6.25% SF | 3624 ± 381 | 72% |
| Medium + PWM +12.5% SF | 4474 ± 306 | 66% |
| Medium + PWM +25% SF | 5095 ± 352 | 61% |

TABLE II

Inhibition of proliferative response of peripheral
blood mononuclear leukocytes to CON A, by SF produced
by the Jurkat, HPB-All and Molt 4 lines

PROLIFERATIVE RESPONSES (CPM)

| % SF (v/v) | Jurkat CPM | % suppression | HPB-All CPM | % suppression | Molt-4 CPM | % suppression |
|---|---|---|---|---|---|---|
| medium | 265 ± 47 | — | 265 ± 47 | — | 265 ± 47 | — |
| medium + CON A | 40792 ± 7959 | — | 40792 ± 7454 | — | 40792 ± 7454 | — |
| medium + CON A +0.015% SF | 3916 ± 239 | 90% | 61751 ± 13610 | — | 14440 ± 6966 | 65% |
| medium + CON A +0.05% SF | 3606 ± 379 | 91% | 31713 ± 11104 | 22% | 4814 ± 580 | 88% |
| medium + CON A +0.1% SF | 3889 ± 413 | 90% | 12399 ± 2129 | 69% | 4126 ± 681 | 90% |
| medium + CON A +0.5% SF | 4489 ± 649 | 89% | 6414 ± 1356 | 84% | 3233 ± 688 | 92% |
| medium + CON A 0.95% SF | 3671 ± 294 | 91% | 3886 ± 1055 | 90% | 2718 ± 910 | 93% |
| medium + CON A +1.9% SF | 3615 ± 211 | 91% | 3678 ± 765 | 91% | 2244 ± 446 | 94% |
| medium + CON A +3.75% SF | 3649 ± 350 | 91% | 3879 ± 734 | 90% | 26622 ± 401 | 93% |
| medium + CON A +15% SF | 3605 ± 191 | 91% | 3421 ± 404 | 92% | 1729 ± 108 | 96% |
| medium + CON A +30% SF | 3862 ± 381 | 91% | 3637 ± 296 | 91% | 855 ± 48 | 98% |

TABLE IV

Inhibition by SF produced by the Jurkat tumor cell lines, of the proliferative responses of human peripheral blood mononuclear leukocytes to allogeneic cells in mixed lymphocyte culture

| | PROLIFERATIVE RESPONSES (CPM) Jurkat | |
|---|---|---|
| % SF (v/v) | CPM | % suppression |
| Medium | 7382 | — |
| Medium + 1.56% SF | 3849 | 48% |
| Medium + 3.12% SF | 3229 | 56% |
| Medium + 6.25% SF | 3922 | 47% |
| Medium + 12.50% SF | 3678 | 50% |
| Medium + 25.00% SF | 6159 | 17% |

TABLE V

Inhibition of de novo immunoglobulin synthesis and secretion of human peripheral blood mononuclear leukocytes in the PWM-induced differentiation system, by SF produced by the Jurkat, HPB-ALL, Molt-4, K562 and CESS CELL LINES.

| | Cell line Supernatants Dilutions | Immunoglobulin* | | |
|---|---|---|---|---|
| | | IgM (microg/dl) | IgA (microg/dl) | IgG (microg/dl) |
| Mononuclear cells + PWM | None | 243.0 | 70.5 | 54.3 |
| | Jurkat | | | |
| MNC + PWM | 1:3 | 19.0 | l.t. 2.0 | <2.0 |
| MNC + PWM | 1:50 | 20.5 | l. t. 2.0 | ND |
| MNC + PWM | 1:1000 | 15.0 | 3.75 | ND |
| MNC + PWM | 1:10000 | 19.0 | 4.5 | ND |
| | HPB-ALL | | | |
| MNC + PWM | 1:3 | 10.5 | l.t. 2.0 | l.t. 2.0 |
| MNC + PWM | 1:50 | 35.0 | 5.7 | l.t. 2.0 |
| MNC + PWM | 1:1000 | 27.3 | 11.3 | l.t. 2.0 |
| MNC + PWM | 1:10000 | 22.3 | 13.0 | l.t. 2.0 |
| | Molt-4 | | | |
| MNC + PWM | 1:3 | 23.5 | l.t. 2.0 | ND |
| MNC + PWM | 1:50 | 36.7 | 14.3 | l.t. 2.0 |
| MNC + PWM | 1:1000 | 35.7 | 16.0 | l.t. 2.0 |
| | K562 | | | |
| MNC + PWM | 1:3 | 9.9 | l.t. 2.0 | ND |
| MNC + PWM | 1:50 | 17.8 | l.t. 2.0 | l.t. 2.0 |
| MNC + PWM | 1:1000 | 18.3 | 9.0 | ND |
| | CESS | | | |
| MNC + PWM | 1:3 | 12.2 | l.t. 2.0 | 10.3 |
| MNC + PWM | 1:50 | 18.0 | l.t. 2.0 | ND |
| MNC + PWM | 1:1000 | 18.3 | 11.2 | ND |

Determined by ELISA
ND - not determined l.t. - less than

TABLE VI

The viability of peripheral blood mononuclear leukocytes is not affected by prolonged incubation with SF produced by the Jurkat* tumor cell lines

| | % Viability Duration of treatment | | | |
|---|---|---|---|---|
| Tumor cell lines | 20 hrs | 44 hrs | 68 hrs | 88 hrs |
| Medium * alone | 98% | 100% | 96% | 93% |
| Jurkat | 99% | 96% | 95% | 90% |

* This effect is also seen with HPB-ALL, K562 and Molt-4 supernatants.

TABLE VII

Suppressor factor(s) preparations produced by the Jurkat cell lines do not affect natural killer cytotoxicity: mediated by peripheral blood mononuclear leukocytes, against K562 targets

| | % Cytotoxicity Effector to target ratio | | | |
|---|---|---|---|---|
| | Donor 1 | | Donor 2 | |
| SF Source | 50:1 | 25:1 | 50:1 | 25:1 |
| Medium | 66 | 59 | 58 | 50 |
| Jurkat | 68 | 56 | 51 | 40 |

TABLE VIII

Inhibition of the growth of human lung tumor cell lines by SF - containing supernatants from the Jurkat, HPB-ALL, K562 and Molt-4 human tumor cell lines

| | Cell Numbers Lines | | | | | |
|---|---|---|---|---|---|---|
| | SK-LC-6 | | | SK-LC-14 | | |
| | Hours of Treatment | | | Hours of Treatment | | |
| Supernatants* | 0 | 60 | 90 | 0 | 60 | 90 |
| None | $0.5 \times 10^5$ | $1.4 \times 10^5$ | $5.7 \times 10^5$ | $0.5 \times 10^5$ | $1.7 \times 10^5$ | $4.2 \times 10^5$ |
| Jurkat | $0.5 \times 10^5$ | $0.6 \times 10^5$ | $1.5 \times 10^5$ | $0.5 \times 10^5$ | $1.4 \times 10^5$ | $1.9 \times 10^5$ |
| HPB-All | $0.5 \times 10^5$ | $1.1 \times 10^5$ | $1.4 \times 10^5$ | $0.5 \times 10^5$ | $2.1 \times 10^5$ | $3.0 \times 10^5$ |
| K562 | $0.5 \times 10^5$ | $0.6 \times 10^5$ | $1.2 \times 10^5$ | $0.5 \times 10^5$ | $0.7 \times 10^5$ | $2.0 \times 10^5$ |

TABLE VIII-continued

Inhibition of the growth of human lung tumor cell lines by SF - containing supernatants from the Jurkat, HPB-ALL, K562 and Molt-4 human tumor cell lines

| | Cell Numbers Lines | | | | | |
|---|---|---|---|---|---|---|
| | SK-LC-6 | | | SK-LC-14 | | |
| | Hours of Treatment | | | Hours of Treatment | | |
| Supernatants* | 0 | 60 | 90 | 0 | 60 | 90 |
| Molt-4 | $0.5 \times 10^5$ | $0.7 \times 10^5$ | $2.7 \times 10^5$ | ND | | |

*These were used at a dilution of 30% (v/v).

TABLE IX

INHIBITION OF THE IN VIVO PRIMARY ANTIBODY RESPONSE OF C3H MICE TO SHEEP ERYTHROCYTIES BY THE 160(36(38F3)) SUPRESSOR FACTOR

| | Plaque forming cells per $1 \times 10^6$ splenocytes* | | | |
|---|---|---|---|---|
| | Exp. 1 | Exp. 2 | Exp. 3 | Exp. 4 |
| No immunization | 17 ± 23 | 29 ± 9 | 13 ± 12 | 35 ± 23 |
| Sheep erythrocytes | 842 ± 6 | 1092 ± 86 | 838 ± 59 | 715 ± 14 |
| Sheep erythrocytes plus 160(36(38F3))* | 408 ± 77** | 117 ± 13** | 96 ± 7** | 216 ± 16** |
| Sheep erythrocytes plus 169(36(38F3))* | 832 ± 56 | 936 ± 71 | 1010 ± 17 | 811 ± 7 |
| Sheep erythrocytes plus Jurkat* | ND | 93 ± 9** | 114 ± 24** | 111 ± 3** |

*C3H mice were immunized i.p. with sheep erythrocytes and received (i.v.) on day 1 2.5 suppressor factor units (SFU) from a purified suppressor factor preparation, in a total volume of 50 microliters. Suppressor factor injections (2.5 SFU per injection) were also given i.v. on days 2, 3, and 4. The animals were sacrificed on day 5, the spleens were removed, lymphocytes were prepared and plaque forming cells were determined. A suppressor factor unit (SFU) was defined as the reciprocal of the maximum dilution that inhibited by 50% of the proliferative response of human peripheral blood mononuclear leukocytes to PHA.
**Statistically significant inhibition was observed (p at least less than 0.005).

TABLE X

INHIBITION OF PROLIFERATION OF PURIFIED LEUKEMIC B CELLS FROM PATIENTS WITH CHRONIC LYMPHOCYTIC LEUKEMIA BY SUPPRESSOR FACTORS PRODUCED BY HUMAN T-T CELL HYBRIDOMAS AND THE JURKAT T-CELL LINE

| Stimulatory Agents(s) | Suppressor Factor | Proliferation Response (cpm) |
|---|---|---|
| PATIENT 1 | | |
| None | None | 977 |
| None | 153(36(38F3)) | 99 |
| BCGF (1:32)+anti-μ | None | 54,121 |
| BCGF (1:32)+anti-μ | 153(36(38F3)) | 194 |
| SAC (1:2000) | None | 855 |
| SAC (1:2000) | 153(36(38F3)) | 126 |
| BCGF (1:32)+anti-μ +SAC (1:2000) | None | 64,924 |
| BCGF (1:32)+anti-μ +SAC (10:2000) | 153(36(38F3)) | 192 |
| PATIENT 2 | | |
| None | None | 3,491 |
| None | 160(36(38F3)) | 206 |
| BCGF (1:32)+anti-μ | None | 14,399 |
| BCGF (1:32)+anti-μ | 160(36(38F3)) | 177 |
| BCGF (1:32)+anti-μ | Jurkat | 187 |

TABLE XI

EFFECT OF SUPPRESSOR FACTORS ON COLONY FORMATION BY HUMAN HEMOPOIETIC PROGENITOR CELLS

| | | Colonies/Clusters per $10^5$ Non-adherent Low Density Normal Human Bone Marrow Cells | | | | | |
|---|---|---|---|---|---|---|---|
| Suppressor Factor** | Final Dilution | Day 7 CFU-GM Colonies | Day 7 CFU-GM Colonies + Clusters | Day 14 CFU-GM Colonies | Day 14 BFU-E Colonies #1 | Day 14 BFU-E Colonies #2 | Day 14 CFU-GEMM Colonies |
| Control | Medium | 61 ± 4 | 111 ± 8 | 59 ± 2 | 37 ± 2 | 49 ± 5 | 8 ± 1 |
| 160 | 1/20 | 50 ± 2 | 107 ± 7 | 56 ± 3 | 35 ± 3 | 47 ± 1 | 7.5 ± 0.5 |
| | 1/100 | 57 ± 6 | 111 ± 14 | 58 ± 1 | 41 ± 2 | 49 ± 1 | 8 ± 1 |
| | 1/1000 | 62 ± 3 | 113 ± 5 | 59 ± 4 | 42 ± 3 | 52 ± 3 | 7.5 ± 1.5 |
| 169 | 1/20 | 58 ± 5 | 114 ± 10 | 58 ± 3 | 35 ± 3 | 47 ± 2 | 9 ± 1 |
| | 1/100 | 63 ± 6 | 111 ± 3 | 58 ± 6 | 40 ± 5 | 52 ± 2 | 8 ± 1 |
| | 1/1000 | 57 ± 4 | 106 ± 5 | 56 ± 3 | 39 ± 1 | 50 ± 5 | 9 ± 2 |
| Jurkat | 1/20 | 63 ± 4 | 112 ± 3 | 23 ± 5 | 28 ± 3 | 48 ± 3 | 8 ± 1 |
| | 1/100 | 64 ± 7 | 109 ± 5 | 65 ± 5 | 37 ± 3 | 52 ± 3 | 8 ± 0 |
| | 1/1000 | 61 ± 5 | 110 ± 4 | 60 ± 4 | 40 ± 1 | 49 ± 3 | 8 ± 2 |
| 160 pI 4.7 | 1/100 | 64 ± 4 | 111 ± 3 | 59 ± 2 | 38 ± 1 | 52 ± 4 | 8.5 ± 0.5 |
| | 1/1000 | 62 ± 2 | 111 ± 1 | 60 ± 3 | 41 ± 3 | 53 ± 3 | 8.5 ± 0.5 |
| | 1/10000 | 57 ± 4 | 114 ± 4 | 62 ± 4 | 42 ± 3 | 54 ± 4 | 7.5 ± 0.5 |

TABLE XI-continued

EFFECT OF SUPPRESSOR FACTORS ON COLONY FORMATION BY HUMAN HEMOPOIETIC PROGENITOR CELLS

| | | Colonies/Clusters per $10^5$ Non-adherent Low Density Normal Human Bone Marrow Cells | | | | | |
|---|---|---|---|---|---|---|---|
| Suppressor Factor** | Final Dilution | Day 7 CFU-GM Colonies | Day 7 CFU-GM Colonies + Clusters | Day 14 CFU-GM Colonies | Day 14 BFU-E Colonies #1 | Day 14 BFU-E Colonies #2 | Day 14 CFU-GEMM Colonies |
| 160 pI 5.7 | 1/100 | 64 ± 5 | 111 ± 4 | 60 ± 7 | 39 ± 2 | 47 ± 2 | 7.5 ± 0.5 |
| | 1/1000 | 60 ± 3 | 108 ± 1 | 59 ± 2 | 41 ± 5 | 53 ± 3 | 9 ± 1 |
| | 1/10000 | 58 ± 2 | 110 ± 3 | 60 ± 5 | 37 ± 4 | 47 ± 3 | 10 ± 2 |

Results are expressed as mean +/− 1 S.E.M. for 3 plates/pt for CFU-GM and 2 plates/pt for BFU-E/CFU-GEMM assays. See Broxmeyer et. al., J. Immunol. 135:2502-2506, 1986 for exact details of methods. In Brief: (1) CFU-GM assay was performed in 0.3% Agar with 10% v/v 5637 CM. Colonies were 50 cells/aggregate and clusters were 3-50 cells/aggregate. Only colonies were scored on day 14 since colonies were large and clusters difficult to distinguish. (2) BFU-E assays were performed in 0.3% methylecellulose with either 0.5 units Toyoba Erythropoietin plus 0.1 mM hemin (=BFU-E #1) or with erythropoietin, hemin and 10% v/v 5637 CM (=BFU-E #2) BFU-E #1 may be more mature than BFU-E #2. CFU-GEMM were scored on same plates as BFU-E #2. Cultures were incubated at 37° C. in low (5%) oxygen tension.
**Partially purified preparations by ammonium sulfate precipitation of the 160, 169 and Jurkat suppressor factors were used. Also highly purified preparations by chromatofocusing of the 160 suppressor factor (two peaks of activity of pI 5.7 and 4.7) were evaluated. These preparations were highly effective in suppressing proliferative responses of human peripheral blood mononuclear leukocytes to PHA dilutions higher than 1:100,000.

TABLE XII

INHIBITION OF PROLIFERATIVE RESPONSES OF BALB/c SPLEEN LYMPHOCYTES TO CON A BY SUPPRESSOR FACTORS PRODUCED BY HUMAN T-T CELL HYBRIDOMAS

| | Counts per minute | | |
|---|---|---|---|
| Suppressor Factor | Medium | Con A 3 μg/ml | Con A 6 μg/ml |
| Control | 3.451 ± 810 | 116,557 ± 20,248 | 82,024 ± 17,853 |
| 160(36(38F3)) | | | |
| 2.5% (v/v) | 5,615 ± 708 | 8,709 ± 573 | 9,656 ± 804 |
| 5% | 5,835 ± 370 | 8,174 ± 922 | 8,954 ± 520 |
| 10% | 5,750 ± 1,266 | 7,312 ± 1,565 | 8,041 ± 458 |
| 20% | 5,628 ± 814 | 6,260 ± 1,042 | 5,864 ± 669 |
| 159(36(38F3)) | | | |
| 2.5% (v/v) | 7,624 ± 355 | 151,540 ± 4,885 | 100,230 ± 17,377 |
| 5% | 8,778 ± 856 | 126,152 ± 26,677 | 92,750 ± 18,483 |
| 10% | 6,604 ± 552 | 44,436 ± 5,503 | 15,262 ± 4,604 |
| 20% | 2,570 ± 536 | 5,107 ± 1,392 | 4,538 ± 1,991 |
| 169(36(38F3)) | | | |
| 2.5% (v/v) | 7,404 ± 55 | 167,288 ± 2,362 | 99,033 ± 499 |
| 5% | 8,502 ± 1,566 | 141,004 ± 12,097 | 84,857 ± 6,475 |
| 10% | 8,076 ± 883 | 117,821 ± 9,652 | 82,417 ± 6,571 |
| 20% | 3,468 ± 431 | 124,251 ± 8,489 | 104,251 ± 8,489 |
| 77(38F3) | | | |
| 2.5% (v/v) | 7,120 ± 426 | 109,377 ± 4,615 | 86,640 ± 6,361 |
| 5% | 7,905 ± 970 | 141,647 ± 9,880 | 74,975 ± 2,835 |
| 10% | 6,723 ± 970 | 158,123 ± 32,110 | 73,488 ± 4,371 |
| 20% | 4,295 ± 266 | 138,389 ± 26,418 | 110,036 ± 7,561 |
| Jurkat | | | |
| 2.5% (v/v) | 12,721 ± 510 | 3,215 ± 751 | 3,024 ± 1,071 |
| 5% | 7,012 ± 498 | 3,250 ± 138 | 2,941 ± 246 |
| 10% | 3,875 ± 802 | 2,995 ± 246 | 3,390 ± 309 |
| 20% | 3,447 ± 1,044 | 4,226 ± 387 | 3,945 ± 436 |

BALB/c mouse spleen lymphocytes were cultured in RPMI-1640 supplemented with 10% fetal calf serum, HEPES buffer, glutamine and antibodies in flat bottomed microtiter plates with Con A and supernatants containing suppressor factors. After three days 37° C., the cultures were pulsed with $^3$H-thymidine and harvested 18 hrs. later.

TABLE XIII

INHIBITION OF PROLIFERATIVE RESPONSES OF BALB/c MOUSE THYMOCYTES TO CON A BY SUPPRESSOR FACTORS PRODUCED BY HUMAN T-T CELL HYBRIDOMAS

| | Counts per minute | | |
|---|---|---|---|
| Suppressor Factor | Medium | Con A 3 μg/ml | Con A 6 μg/ml |
| Control | 2,276 ± 129 | 180,972 ± 17,909 | 221,760 ± 27,796 |
| 160(36(38F3)) | | | |
| 2.5% (v/v) | 3,307 ± 971 | 3,237 ± 170 | 3,755 ± 106 |
| 5% | 3,088 ± 1,788 | 3,957 ± 1,092 | 4,786 ± 593 |
| 10% | 2,969 ± 940 | 4,977 ± 2,321 | 5,228 ± 325 |
| 20% | 3,571 ± 1,994 | 5,016 ± 938 | 5,536 ± 605 |
| 159(36(38F3)) | | | |

TABLE XIII-continued
INHIBITION OF PROLIFERATIVE RESPONSES OF BALB/c MOUSE THYMOCYTES TO CON A BY SUPPRESSOR FACTORS PRODUCED BY HUMAN T-T CELL HYBRIDOMAS

| Suppressor Factor | Counts per minute | | |
|---|---|---|---|
| | Medium | Con A 3 μg/ml | Con A 6 μg/ml |
| 2.5% (v/v) | 225 ± 19 | 4,132 ± 521 | 15,435 ± 5,486 |
| 5% | 963 ± 128 | 3,271 ± 111 | 3,553 ± 987 |
| 10% | 2,469 ± 294 | 3,050 ± 91 | 2,242 ± 457 |
| 20% | 3,000 ± 84 | 8,295 ± 2,455 | 2,700 ± 211 |
| 169(36(38F3)) | | | |
| 2.5% (v/v) | 2,673 ± 152 | 166,300 ± 19,495 | 247,600 ± 56,223 |
| 5% | 2,088 ± 467 | 180,519 ± 12,662 | 302,994 ± 71,949 |
| 10% | 3,856 ± 428 | 192,006 ± 43,278 | 286,007 ± 57,489 |
| 20% | 4,659 ± 1,279 | 202,671 ± 19,523 | 298,623 ± 16,524 |
| 77(38F3) | | | |
| 2.5% (v/v) | ND | 124,507 ± 18,981 | 234,600 ± 21,645 |
| 5% | | 147,000 ± 29,060 | 208,890 ± 21,563 |
| 10% | | 172,036 ± 38,984 | 293,000 ± 57,384 |
| 20% | | 157,127 ± 40,534 | 235,660 ± 41,730 |
| Jurkat | | | |
| 2.5% (v/v) | 5,568 ± 573 | 5,746 ± 708 | 3,894 ± 513 |
| 5% | 6,705 ± 1,583 | 5,310 ± 441 | 4,039 ± 629 |
| 10% | 5,546 ± 312 | 7,089 ± 2,124 | 4,626 ± 2,205 |
| 20% | 3,438 ± 596 | 7,335 ± 1,100 | 5,953 ± 2,542 |

BALB/c thymocytes were cultured in RPMI-1640 supplemented with 10% fetal calf serum HEPES buffers glutamine and antibodies in flat bottomed microtiter plates with Con A and supernatants containing suppressor factors ($1 \times 10^6$ cells per well in 200 microliters). After three days at 37° C. the cultures were pulsed with $^3$H-thymidine and harvested 18 hrs. later.

MATERIALS AND METHODS

Isolation of peripheral blood mononuclear leukocytes and depletion of monocytes. Mononuclear cells from normal donors were isolated by centrifugation on a Ficoll/Hypaque density cushion (Boyum, A. (1968) Scand. Clin, Lab. Invest. 21:(Suppl. 97) 77), at room temperature. The cell were washed three times in Hanks, balanced salt solution (HBSS) and resuspended in RPMI-1640 containing 15% heat-inactivated fetal calf serum at a concentration of $4 \times 10^6$ cells/ml. Lymphocyte separator reagent (Technicon Instrument Co., Tarrytown, N.Y.) was added to the mononuclear cell suspension at a volume ration of 1:2 and the mixture was incubated at 37° C. on a rotator for 30 min. Phagocytic cells were depleted by subsequent centrifugation at $400 \times g$ for 20 min on a Ficoll/Hypaque density cushion. Lymphoid cells depleted of phagocytic cells were collected from the interface, washed three time with Hank's balanced salt solution (HBSS) and resuspended at $4 \times 10^6$ cells/ml.

Preparation of T lymphocytes. T lymphocytes were prepared by rosetting with neuraminidase-treated sheep erythrocytes (SRBC) (25 units/ml of 5% SRBC) followed by centrifugation on Ficoll/Hypaque as previously described [Platsoucas et al. (1980) J. Immunol. 125:1216]. Two-milliliter aliquots of lymphocytes ($4 \times 10^6$/ml) in HBSS were mixed with 0.5 ml of heat-inactivated and SRBC-absorbed fetal calf serum and 2 ml of 1% neuraminidase treated SRBC. The mixture was incubated for 5 min at 37° C., centrifuged for 5 min at $200 \times G$, and incubated at 4° C. for an additional hour. The rosettes were resuspended carefully and incubated on ice for an additional 15 min. The cell suspensions were layered on a Ficoll/Hypaque density cushion and centrifuged at $400 \times G$ for 20 min at controlled temperature (22° C.). Non-T cells were recovered from the interface and were washed three times with HBSS. Rosetting T cells were recovered from the pellets after lysis of attached SRBC by Tris-buffered 0.83% ammonium chloride (pH 7.2). The T cells were washed three times with HBSS. E-rosetting cells prepared by this method were more than 95% T lymphocytes, as determined by rerosetting with SRBC without nonspecific esterase-positive cells and less than 2% immunoglobulin-bearing cells. E-rosette-negative cells contained more than 70% surface immunoglobulin cells, as determined by immunofluorescence, and less than 1% of E-rosette forming cells or non-specific esterase positive cells. These cells were used as B cells. B cells are used for B cell growth factor assay.

Proliferative response to mitogens. Human peripheral blood mononuclear leukocytes (at a concentration of $1 \times 10^6$ cells/ml) were cultured in RPMI-1640 containing 10% fetal calf serum and supplemented with 25 mM Hepes, 2 mM L-glutamine and 100 units/ml Penicillin and 100 micrograms/ml streptomycin. One hundred microliters of the cell suspension were stimulated on U-microliter plates (Scientific Products) by various concentration of mitogens (PHA-P, Con A, PWM) at 37° C. in a humidified incubator in a 5% $CO_2$, 95% air environment. The cultures were pulsed with 25 microliters of tritiated thymidine (specific activity, 6.7 Ci/mmol, New England Nuclear, Boston, Mass.) after 72 hours and harvested using an automatic cell harvester 24 hour after the addition of the isotopes.

Mixed lymphocyte culture. Human peripheral blood mononuclear leukocytes from various donors were prepared as above.

Responding cells ($1 \times 10^5$) were cultured with $1 \times 10^5$ stimulating cells in round bottom microtiter plates in total volume of 0.2 ml. The stimulating cells were inactivated by x-irradiation (2000 rads). The culture medium is RPMI-1640 supplemented with 10% fetal calf serum, 25 mM Hepes, 2 mM L-glutamine, penicillin (100 units/ml) and streptomycin (100 microgram/ml). The cultures were incubated at 37° C. in a humidified atmosphere with 5% $CO_2$, pulsed the 5th day with 1 micro Ci/well of $^3$H-thymidine (New England Nuclear, Boston, Mass., specific activity 6.7 Ci/mmole) (Skarton, Norway). All cultures were performed in quadruplicate.

Natural killer cytotoxicity. Natural killer cytotoxicity was determined as previously described (Platsoucas, et al. (1980) J. Immunol. 125:1216). Target cells of the K562 and Molt-4 lines, maintained in RPMI-1640 supplemented with 10% fetal calf serum, glutamine and antibiotics as above were labelled with 300 microliters of $^{51}$Cr per $2\times10^6$ cells [sodium ($^{51}$Cr) chromate, New England Nuclear, Boston, Mass.] for 2 hours. The target cells were washed three times and then resuspended in the same medium, at a concentration of $5\times10^4$ cells/ml. Effector lymphocytes were washed three times in RPMI-1640 supplemented with 10% fetal calf serum, arranged at the appropriate concentration and one hundred microliters were added to one hundred microliters of target cells in U-bottom microtiter plates (Nunclon, Denmark), to achieve effector to target ratios 100:1, 50:1, and 25:1 etc. The plates were centrifuged at $40\times g$ for 2 min and subsequently incubated at 37° C. in a humidified 5% $CO_2$ atmosphere. After 4 hours, the plates were centrifuged at $500\times g$ for 5 min and 100 microliters of the supernatants were collected and counted for $^{51}$Cr release in a well-type Auto Gamma scintillation counter.

Percent specific lysis is calculated by the formula:

$$\% \text{ Specific lysis} = \frac{E - S}{T - S} \times 100$$

where E=mean cpm released in the presence of effector cells. S=mean cpm spontaneously released by target cells incubated with medium alone, and T=mean cpm released after treating target cells with Triton $\times 100$ (1:100 dilution).

Cell viability. Peripheral blood mononuclear leukocytes (MNL) were cultured at a concentration of $1\times10^6$ cells/ml in RPMI 1640 supplemented with 10% heat-inactivated FCS, 25 mM herpes buffer, 2 mM L-glutamine, and the antibiotics streptomycin 100 micrograms/ml and penicillin 100 U/ml for up to 88 hrs.

Control samples were incubated in the above medium and test samples are incubated with SF produced by Jurkat et al cell lines. Samples were withdrawn at 20 hrs, 44 hr, 68 hrs and 88 hrs. Cells were washed $2\times$ and viability was determined by Trypan blue dye exclusion.

Origin of cells. Cell line used in the specification were established cell lines from patients with various leukemias.

M.W. Determinations. These were carried out by AcA-44 ultrogel (LFB) filtration in isotonic phosphate buffered saline (PSB). Molecular weight markers employed involved:

| Bovine serum albumin | 68,000 M.W. |
| Ovalbumin | 43,000 M.W. |
| Cytochrome c | 11,700 M.W. |

Induction of de novo Ig synthesis and secretion by human peripheral blood mononuclear leukocytes in the PWM-induced differentation cysts. Human peripheral blood mononuclear leukocytes were cultured at $1\times10^6$ cells/ml in RPMI-1640 supplemented with 10% heat inactivated fetal calf serum, 2 mM glutamine, Hepes and antibiotics as previously described, in total volume of 2 ml, for 7 days at 37° C. in 5% $CO_2$ in a humidified incubator. Pokeweed mitogen (10 microgram/ml, optimal concentration; Grand Island Biological Co., Grand Island, N.Y.) was added from the beginning of the culture. After incubation for 7 days the tubes were centrifuged at $400\times g$ and supernatants were carefully withdrawn and stored at $-20°$ C. until assayed for immunoglobulin.

Determination of de Novo IgG, IgA, IgM immunoglobulins by enzyme-linked immunoabsorbent assay (ELISA). These determinations were carried out by a modification of the method described by Engvall and Perlmann J. Immunol. 109:129 (1972). Rabbit anti-human immunoglobulin antibody, heavy chain specific (mu, gamma or alpha) (Accurate Chemical) were arranged at a concentration of 5 g/ml in 0.10M $Na_2CO_3$, pH 9.6, containing 0.05% sodium azide. Two hundred microliters of antibody solution per well were transferred into 96-well round bottom microliter plates and incubated at 37° C. for 3 hours. The plates were stored at 4° C. until use and were stable for over two weeks. Before use the plates were washed with PBS containing 0.02% Tween 20 three times and were allowed to remain at room temperature for 5 min, between washings. Several dilutions of the unknown immunoglobulin containing supernatants were prepared in PBS containing 0.02% Tween 20 and volumes of 0.2 ml will be transferred to the plates. The plates were incubated for 5 hours at room temperature, on a rocket platform.

Supernatants were removed by aspiration and the tubes were washed three times with PBS, containing 0.02% Tween 20. Alkaline phosphatase conjugated rabbit anti-human immunoglobulin antibody heavy chain specific was obtained from AMP Immunoreagents Inc., Sequin, Tex. (gamma° mu°, or alpha° heavy chain specific). Before use the conjugates were absorbed with 1% ovalbumin solution in phosphate buffered saline (1 hour at room temperature), to absorb extra gluteraldehyde. One ml of conjugate diluted 1:500 with PBS - Tween 20, was added to the anti-human Ig-human Ig coated tubes, and the tubes were incubated for 16 hours at room temperature. Subsequently, the unbound conjugate was removed by washing the plates three times with PBS Tween 20. The amount of bound alkaline phosphatase rabbit anti-human heavy chain specific, was determined using p-nitrophenylphosphate (NPP) (Sigma) as a substrate. One ml of 1 mg/1 NPP, in 0.05M sodium carbonate buffer (pH 9.8) containing $10^{-3}$M $MgCl_2$ was added to the plates and the released p-nitrophenolate was measured at 405 nm after one hour, using a titertek ELISA reader. Standard curves were constructed using purified IgG, IgA or IgM immunoglobulins for polyclonal immunoglobulin secretion, or purified paraproteins from patients with multiple myeloma for the determination of idiotypic immunoglobulin secretion.

PBS=phosphate buffered saline

Inhibition of the growth of human tumor cell lines by supernatants containing the SF. Cells from human tumor lung lines were arranged at a concentration of $5\times10^4$ cells/ml, in Minimal Essential Medium supplemented with 10% heat-inactivated fetal calf serum, 2 mM L-glutamine and antibiotics (streptomycin 100 microgram/ml and penicillin 100 U/ml). One ml of cell suspension was transferred to 24 well plates. Cultures were set up in triplicate. After the cells were attached, supernatants containing SF(s) were added. After 60 and 90 hours in culture, the cells were detached with EDTA (final concentration 0.28%) and counted. Isolation of suppressor factor(s). Supernatants containing suppressor factors are first concentrated using either ammonium sulfate precipitation (80%) (by the method described by Dixon, Biochem. J. 54:457, 1953) or concentration by Amicon ultrafiltration. Subsequently the concentrated factor preparation is subject to gel filtration or ionic exchange DEAE-high pressure liquid chromatography (HPLC) or preparative chromatofocusing. These isolation procedures can also be applied sequentially.

Figure 1B:
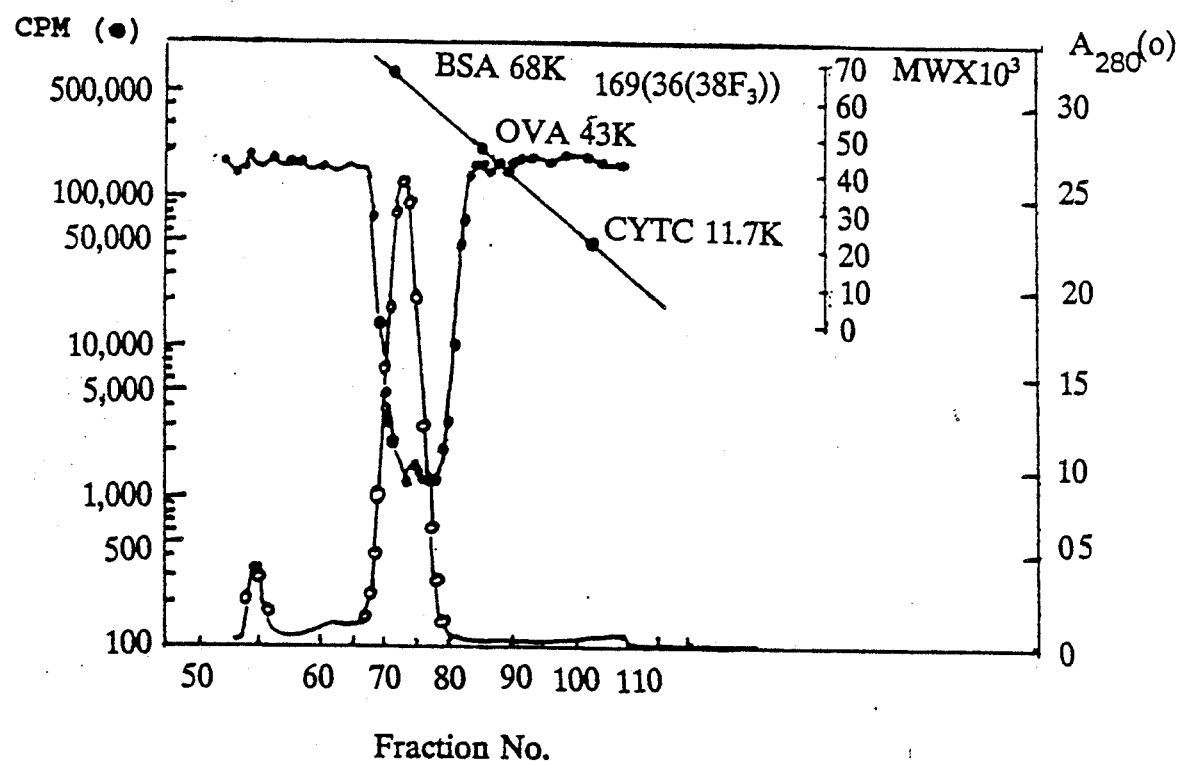
Figure 1C:
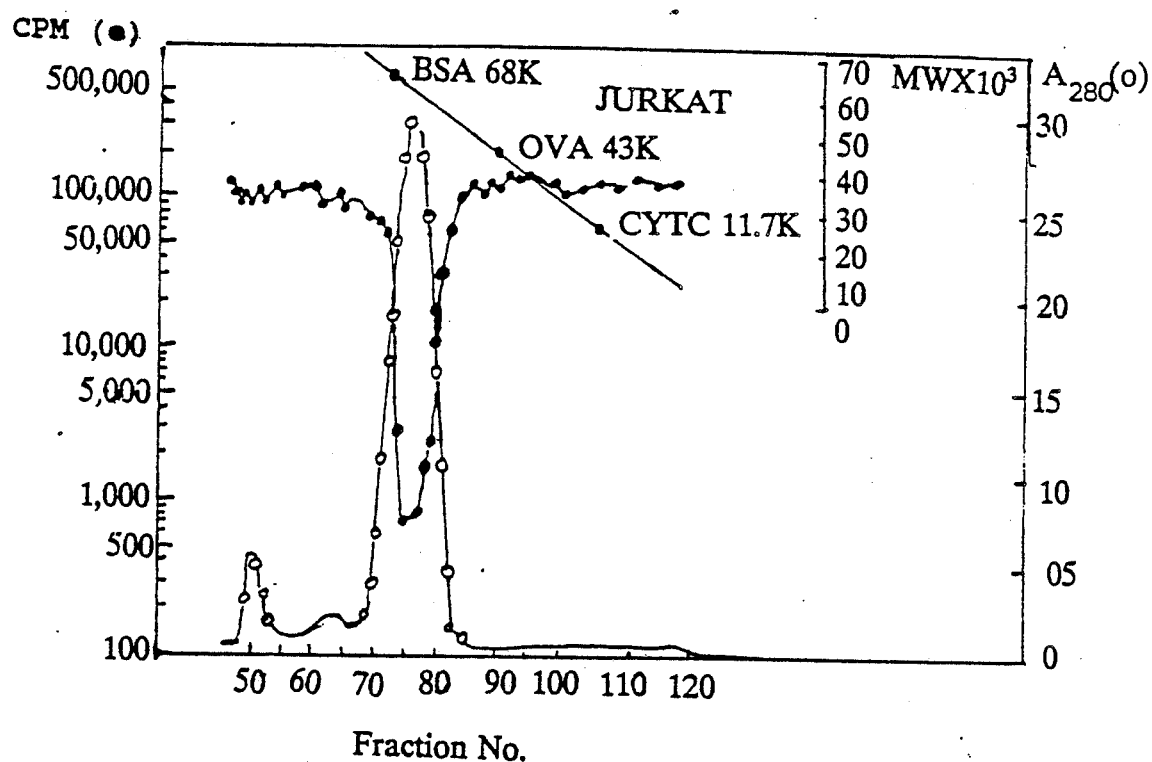

Gel filtration of the 160, 169, 153 and Jurkat suppressor factors was carried out by standard procedures using ACA-44 ultragel (LKB, Bromma, Sweden). Representative results are shown in FIG. 1. These factors had a molecular weight in the range of 50,000–70,000.

Figure 2:
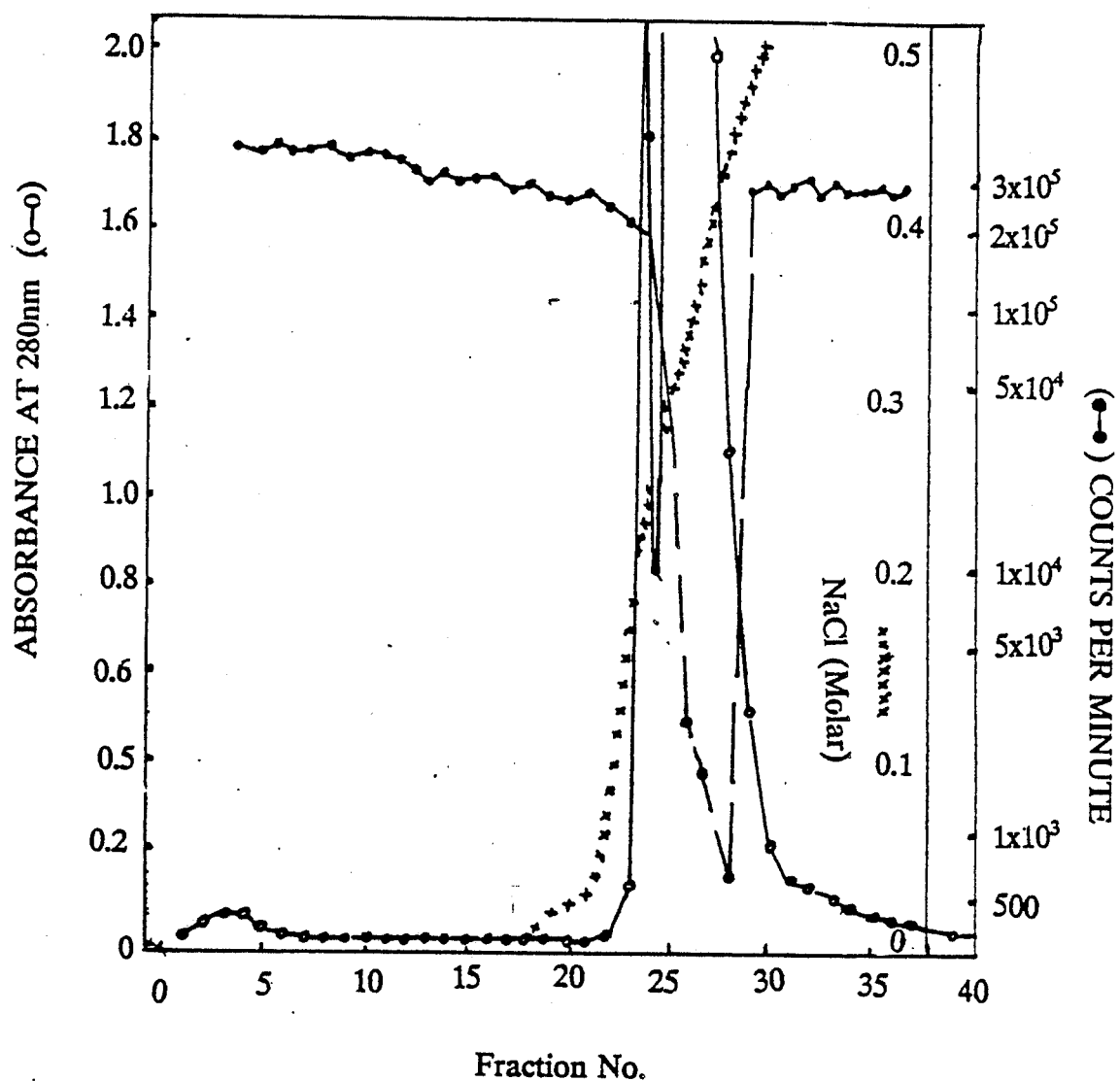
FIG. 2 shows fractionation of the 160 suppressor factor by anion exchange DEAE-HPLC. The hollow dot line represents absorbance at 280 nm and the solid dot line represents suppression of proliferative response.

Studies were carried to purify further these factors by ionic exchange HPLC using protein PAK DEAE 5PW columns, by the method of Strahler et al. (J. Chromatography 266:281, 1983). Representative results are shown in FIG. 2. Elution of the suppressive activity was achieved by using a linear gradient of 0.02M. tris, pH 7.8 to 0.02M tris, pH 7.8, 0.5M NaCl. The suppressive activity of the 160 factor was eluted from the column by 0.35M NaCl. The 169 suppressor factor exhibited a similar elution profile.

Chromatofocusing (Sluyterman and Elgersman, J. Chromatography 150:17, 1978); Sluyterman and Wijdenes, J. Chromatography 150:31, 1978) of the suppressor factors was carried out by applying solubilized precipitates obtained from ammonium sulfate concentrated suppressor factor or suppressor factor preparations purified by the methods described above [dialyzed against 25 mM imidazole (Aldrich), pH 7.4 for 24 hr at 4° C.] to Polybuffer Exchanger 94 (PBE 84) ionic exchange media (Pharmacia) equilibrated with imidazole buffer]. The flow rate during loading of the column with suppressor factor and focusing was 50 ml/cm²/hr and it was generated using a 2132 microperpex peristaltic pump. Focusing was carried out using polybuffer 74 (PB 74), pH 3.80, to facilitate the formation of a linear pH gradient. The focused material eluted from the column was collected in 5 ml fractions or less using a 2211 superac fraction collector and a 2238 Uvicord SII continuous flow spectrometer to measure eluent optical density at 280 nm (LKB). The pH of each collected fraction was determined and the endpoint of the chromatofocusing run was identified when the pH of the eluent reached the pH of PB 74 (pH 3.8). The fractions were brought to pH of 7.2, and their ability to suppress proliferative responses of PBMC to PHA was tested.

Chromatofocusing analysis of the 160 suppressor factor revealed activity peaks at isoelectric points of 4.7 and 5.7. The 169 suppressor factor revealed one peak of activity at isoelectric point of 4.7. In contrast, the Jurkat-derived suppressor factor exhibited one peak of suppressive activity at isoelectric point of 5.2 (FIG. 3). Inhibition of proliferation (90% or higher) by factor material present in these peaks was evident at a dilution of at least 1:100,000. On the basis of the distinct isoelectric points and their different functional properties (see previous amendments) it was concluded that the hybridoma-derived 160 and 169 factors and the Jurkat derived factor are different.

What is claimed:

1. Purified human suppressor factor isolated from human lymphoblastoid tumor cell supernatant where it is constitutively found and characterized by:
    (a) suppression of mitogen, antigen or alloantigen driven cellular proliferation of human peripheral blood leukocytes;
    (b) suppression of antibody production, synthesis and secretion;
    (c) molecular weight range of 55,000 to 70,000 daltons;
    (d) suppression of cellular proliferative response of T and B cells;
    (e) suppression of cellular proliferative response driven by alloantigens, antigens and mitogens selected from the group consisting of Pokeweed mitogen (PWM), concanavalin A (CON A), phytohemagglutinin (PHA), and mixtures thereof;
    (f) inhibition of proliferative response of human peripheral blood mononuclear leukocytes to allogeneic cells in mixed lymphocyte cultures;
    (g) inhibition of proliferation of tumor cell lines;
    (h) having no effect on natural killer cell cytotoxicity;
    (i) inhibition of antibody production in vitro by human peripheral blood mononuclear leukocytes exposed to PWM;
    (j) not affecting the viability of human peripheral blood mononuclear leukocytes in culture;
    (k) not causing lysis of K-562 leukemic cell targets as determined by chromium release assay; and
    (l) not inducing the differentiation of suppressor T-cells.

2. Method for characterization of a suppressor factor of claim 1 which comprises exposing mitogen treated human peripheral blood mononuclear leukocytes to a lymphoblastoid cell specimen and observing a cellular proliferative response or lack thereof of the mitogen treated human peripheral blood mononuclear leukocytes.

3. Method of claim 2 wherein the mitogen treated human peripheral blood mononuclear leukocytes are treated with a mitogen selected from the group consisting of concanavalin A, pokeweed mitogen, phytohemagglutinin and mixtures thereof.

4. Method of treating leukemia which comprises treating leukemia cells in vitro or in vivo with an effective amount of the suppressor factor of claim 1.

5. Method of treating or preventing graft versus host disease which comprises treating a subject with said disease with an effective amount of the suppressor factor of claim 1.

6. Method of treating a malignancy which comprises treating a subject with said malignancy with an effective amount of the suppressor factor of claim 1.

7. Method of claim 6 wherein the malignancy is a leukemia or a lymphoma.

8. Method of treating transplantation disorder which comprises treating a subject with said disorder with an effective amount of the suppressor factor of claim 1.

9. Method of treating an autoimmune disease which comprises treating a subject with said autoimmune disease with an effective amount of the suppressor factor of claim 1.

10. Method of claim 9 wherein the autoimmune disease is selected from the group consisting of rheumatoid arthritis, systemic lupus erythematosus, myasthenia gravis, multiple sclerosis and allergies.

* * * * *